US00PP16573P3

(12) United States Plant Patent
Whitcomb

(10) Patent No.: US PP16,573 P3
(45) Date of Patent: May 23, 2006

(54) RIVER BIRCH TREE NAMED 'WHIT XXV'

(50) Latin Name: *Betula nigra*
Varietal Denomination: WHIT XXV

(75) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 144 days.

(21) Appl. No.: 10/927,297

(22) Filed: Aug. 26, 2004

(65) Prior Publication Data

US 2006/0048249 P1 Mar. 2, 2006

(51) Int. Cl.
*A01H 5/00* (2006.01)

(52) U.S. Cl. ..... Plt./216
(58) Field of Classification Search ..... Plt./216
See application file for complete search history.

(56) References Cited

U.S. PATENT DOCUMENTS

PP10,963 P 6/1999 Cheng et al. ..... Plt./216
PP12,768 P2 7/2002 Pinney, Jr. ..... Plt./216

OTHER PUBLICATIONS

Midcap, J. Landscape Plants for Georgia, Cooperative Extension Service, Bulletin 625, Revised Apr. 2001, pp. 1 and 35–40 only [online], [retrieved on May 18, 2005]. Retrieved from the Internet <http://pubs.caes.uga.edu/caes-pubs/pubcd/B625.htm>.*
Moon's Tree Farm, Inc. Wholesale Tree Grower, Changing the Landscape of the Landscape Industry, 2 pages [online], [retrieved on May 18, 2005]. Retrieved from the Internet <http://www.moonstreefarm.com/duraheat.htm>.*
Trademark Electronic Search System of DURA–HEAT, 1 page only.*

* cited by examiner

*Primary Examiner*—Anne Marie Grunberg
*Assistant Examiner*—June Hwu
(74) *Attorney, Agent, or Firm*—Streets & Steele; Jeffrey L. Streets; Frank J. Campigotto

(57) ABSTRACT

A new and distinct cultivar of river birch tree, *Betula nigra,* named 'WHIT XXV,' characterized as having a tree form that is broadly pyramidal to oval and may be grown with a single stem or multiple stems for greater landscape appeal. The bark of the 'WHIT XXV' is creamy-white during the late summer, fall and winter, developing its coloration at a young age when most stems are about 0.75 to 1.0 inch in diameter. The leaves are dark green of moderate size and turn yellow-gold in the fall.

5 Drawing Sheets

Genus and species: *Betula nigra.*
Varietal denomination: River Birch 'WHIT XXV'.

BACKGROUND OF THE INVENTION

1. Field of the Invention

This invention relates to a new and distinct variety or cultivar of the deciduous tree, *Betula nigra,* commonly known as river birch.

2. Description of the Related Art

River birch trees are native to stream banks and wet areas over much of the eastern half of the United States extending westward to central and northern Oklahoma. A river birch tree is typically about 30 to 60 feet tall having a broad spreading crown and a short, thick, soon-branching trunk that is rarely larger than between about 12 and 24 inches in diameter. The bark is reddish brown or silvery gray, shiny and becomes fissured, separating into papery scales.

The inventor of this new and distinct river birch gathered a large quantity of seed from the western most native river birch seedlings in central Oklahoma in 1986. but none of these gathered seeds germinated. In 1987, about three pounds of additional seeds were gathered from the western most native birch tree seedlings having the lightest bark in central Oklahoma. These trees were located along a narrow steam that was typically without flowing water for six months or more each year. After planting, only a fraction of the seeds germinated and most of the seedlings were weak and did not survive the first summer. There were, however, three vigorous seedlings that survived and were planted into a field. Two of these seedlings were typical loose, open-branched trees and considered of little value.

The third seedling was more ornamental with denser branching, darker leaves and slightly slower growth. In 1992, when the seedling was six years old, viable seeds were produced. The resulting seedlings from these produced seeds were planted in a field where they grew for five years before producing viable seed. Seed was collected from one of these seedlings having lighter bark than the others. Seedlings from this last collection of seeds were planted and allowed to grow.

The new plant of this invention was one of the seedlings grown from the last collection of seeds and is distinctly different from its ancestors, the parent plant or its other siblings. The new plant is characterized as having creamy-white bark during late summer, fall and winter. The white bark develops at a young age, when most stems are about 0.75 to 1.0 inch in diameter. The leaves are dark green of moderate size and turn yellow-gold in the fall. The color of the bark of a typical river birch tree is a cinnamon tan to light brown. While the bark of some river birch trees develop a creamy tan color on larger stems, the present cultivar differs from other river birch trees known to the inventor as having bark that is creamy-white once the stems start to peel, even at a very young age when the stems have diameters of between about 0.75 and 1 inch.

The river birch that is known to the inventor and appears to be the most similar to that of the claimed river birch tree is the Dura-Heat® river birch tree. However, the Dura-Heat® river birch may be differentiated from the current invention as having bark coloration under the peeling bark that is darker as well as rougher in texture. The rougher texture of the exposed bark under the peeling bark of the Dura-Heat® river birch tree is due to slender pieces of bark that are loose and thereby roughen the bark surface.

This new and distinct plant was first asexually reproduced by rooting softwood cuttings from the original plant near Stillwater, Okla. The asexually reproduced plants show the unique features that characterize this new river birch tree indicating that the unique features of this plant are stable through its successive generations of asexual reproduction.

SUMMARY OF THE INVENTION

The present invention resulted from the discovery of a new and distinct variety of river birch tree, *Betula nigra,* which has been given the cultivar name 'WHIT XXV.' 'WHIT XXV' is characterized as having a tree form that is broadly pyramidal to oval and may be grown with a single stem or multiple stems for greater landscape appeal. The bark of the 'WHIT XXV' is creamy-white during the late summer, fall and winter, developing its coloration at a young age when most stems are about 0.75 to 1.0 inch in diameter. The leaves are dark green of moderate size and turn yellow-gold in the fall.

BOTANICAL DESCRIPTION OF THE PLANT

The following botanical description is of the new and distinct cultivar of the river birch tree, *Betula nigra,* named 'WHIT XXV'. Specific color designations set forth by number designations are in accordance with The Royal Horticultural Society Colour Chart. General color recitations are consistent with ordinary American color terminology.

The river birch tree 'WHIT XXV' has not been observed under all possible environmental conditions. It is to be understood that the phenotype may vary significantly with variations in environment such as soils, temperature, light intensity, and length of day, without any differences in the genotype of the plant. The following botanical characteristics and observations are taken from the plant when grown under normal outdoor conditions in north central Oklahoma. The described plant was about 7 years old growing in a field in north central Oklahoma in September.

The plant:

*Type.*—Woody tree with single or multiple stems.

*Classification.*—River birch tree, *Betula nigra.*

*Growth habit.*—Pyramidal when young, growing more oval with age.

*Origin.*—An open pollinated cross in a birch selection/breeding program in Stillwater, Okla.

*Parentage.*—The parent plant was a third generation seedling from a native river birch tree growing in central Oklahoma. The parent plant originated from seeds taken from seedlings planted in 1992, which originated from seedlings planted in 1987, which originated from seeds collected from the native river birch trees in central Oklahoma. The seeds were gathered selectively from each generation of trees having the whiter bark. The parent plant resulted from these repeated selections of seeds from trees with whiter bark. The parent plant was an unnamed river birch tree that is still growing in a field of trees in north central Oklahoma.

*Propagation.*—The plant is easy to propagate from softwood cuttings taken in May, June or July in north central Oklahoma, with the distinguishing characteristics disclosed herein being firmly fixed and retained through the successive generations of asexual reproduction.

Figure 1:
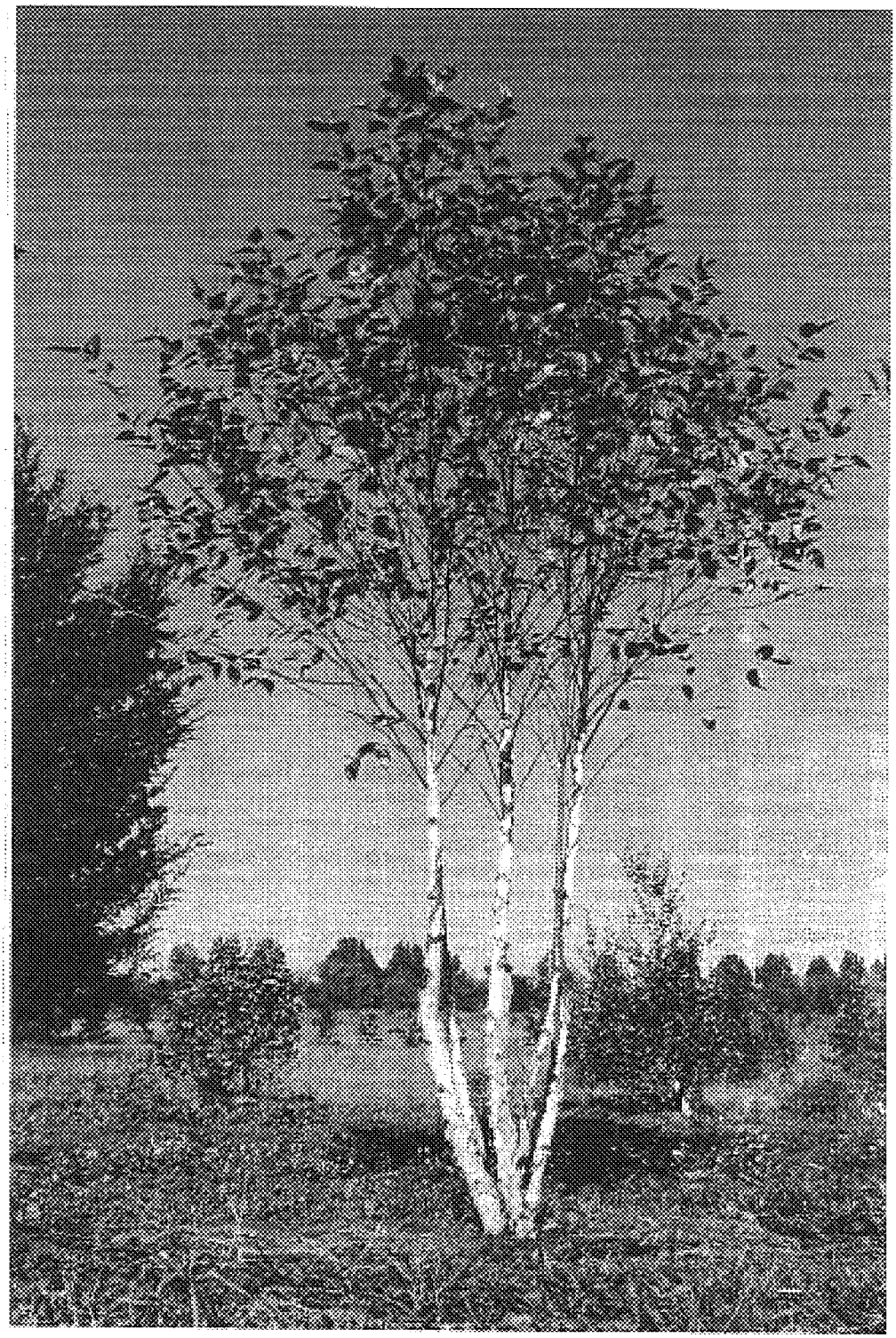
FIG. 1 is a full color photographic view of my new river birch tree.
Figure 2:
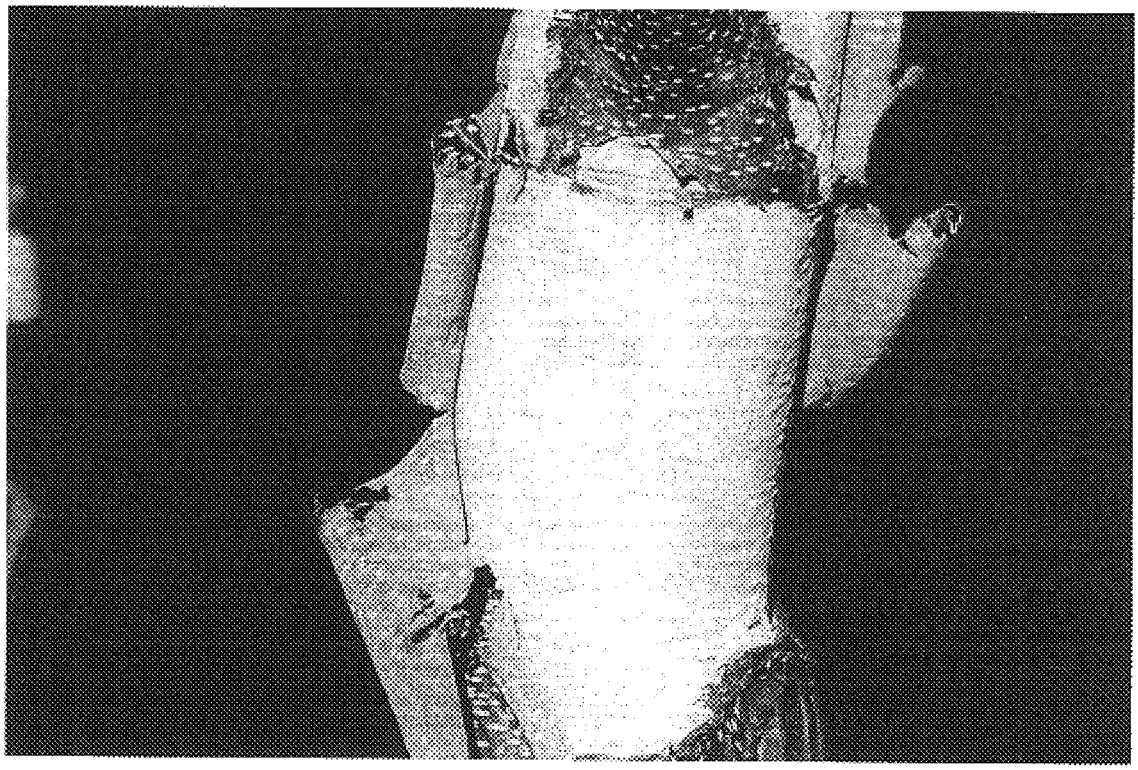
FIG. 2 is a full color photographic view of the creamy-white bark on a 1.5 inch diameter stem of the tree shown in FIG. 1.
Figure 3:
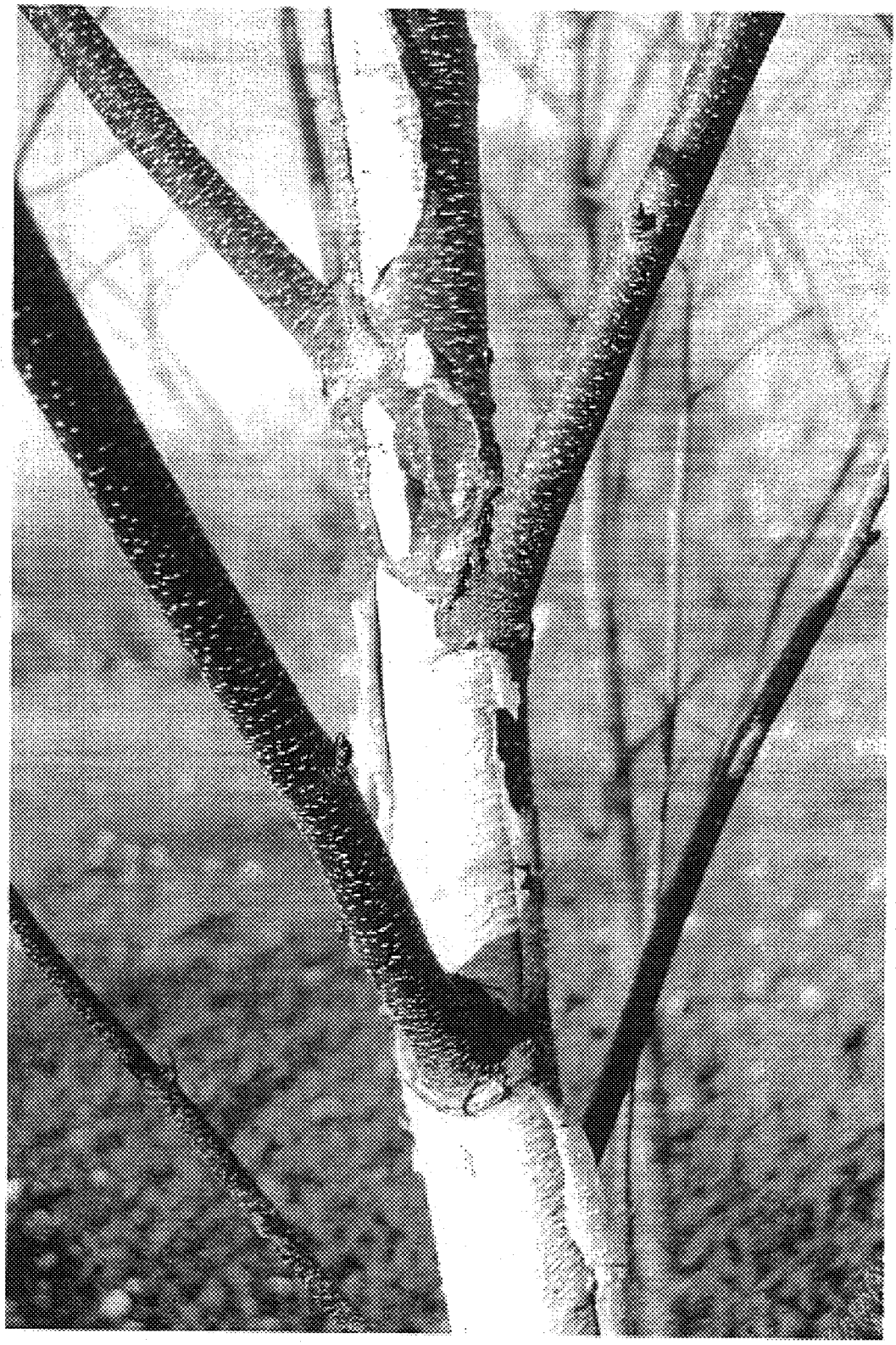
FIG. 3 is a full color photographic view of young bark peeled away to expose the creamy-white inner bark on a stem section measuring about 0.75 inches in diameter at the top of the stem section and about 1.25 inches in diameter at the bottom of the stem section on a typical specimen of my new river birch tree.
Figure 4:
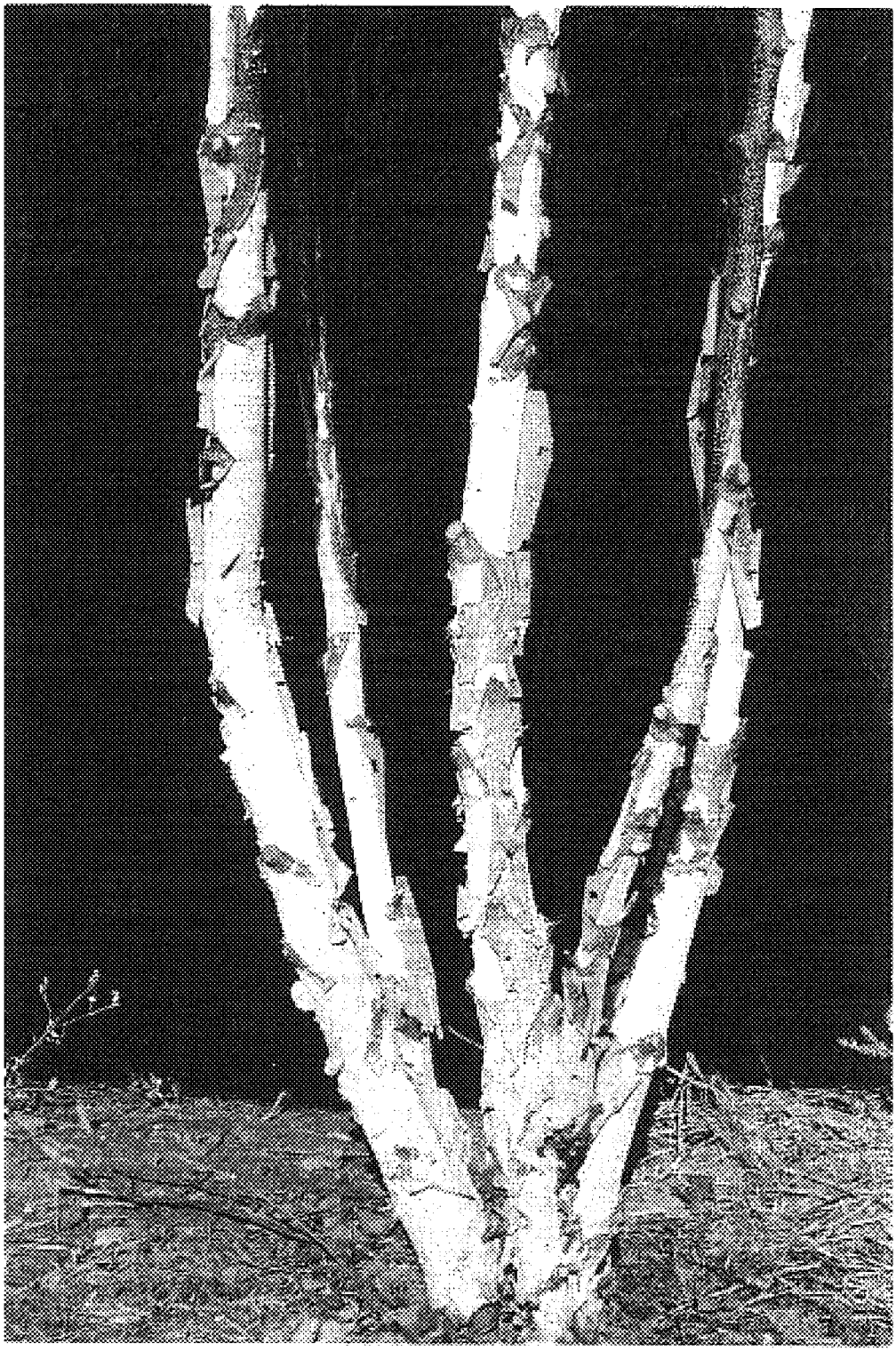
FIG. 4 is a full color photographic view of the bark peeled back on the base stems of the tree shown in FIG. 1 to reveal the creamy-white inner bark.

*Size and shape.*—The growth habit is a treeform that is broad oval. The tree may be grown with either a single stem or, to provide a more ornamental look, may be grown with multiple stems that are created by timely pruning. The growth rate is vigorous in late spring and early summer and continues into mid-summer when moisture is adequate. Branches are produced in abundance and are typically removed from the lower portion of the stem(s) to expose the creamy white bark. In north central Oklahoma, the plant size is characterized as having a height of between about 30 and about 50 feet. The specimen shown in FIG. 1 is approximately 14 feet tall with spread of about 10.5 feet. The broad oval growth habit is not observable in FIG. 1 as the lower limbs have been removed. The four major stems of the illustrated specimen range between about 1.5 and 3 inches.

*Hardiness.*—USDA hardiness zones 5 through 9.

*General health and pest susceptibility.*—The foliage of the river birch 'WHIT XXV' has remained pest free in central Oklahoma. The plant is characterized as being resistant to bronze birch borer and leaf-spot disease.

Foliage:

*Leaf persistence.*—Deciduous.

*Arrangement on stems.*—Alternate.

Figure 5:
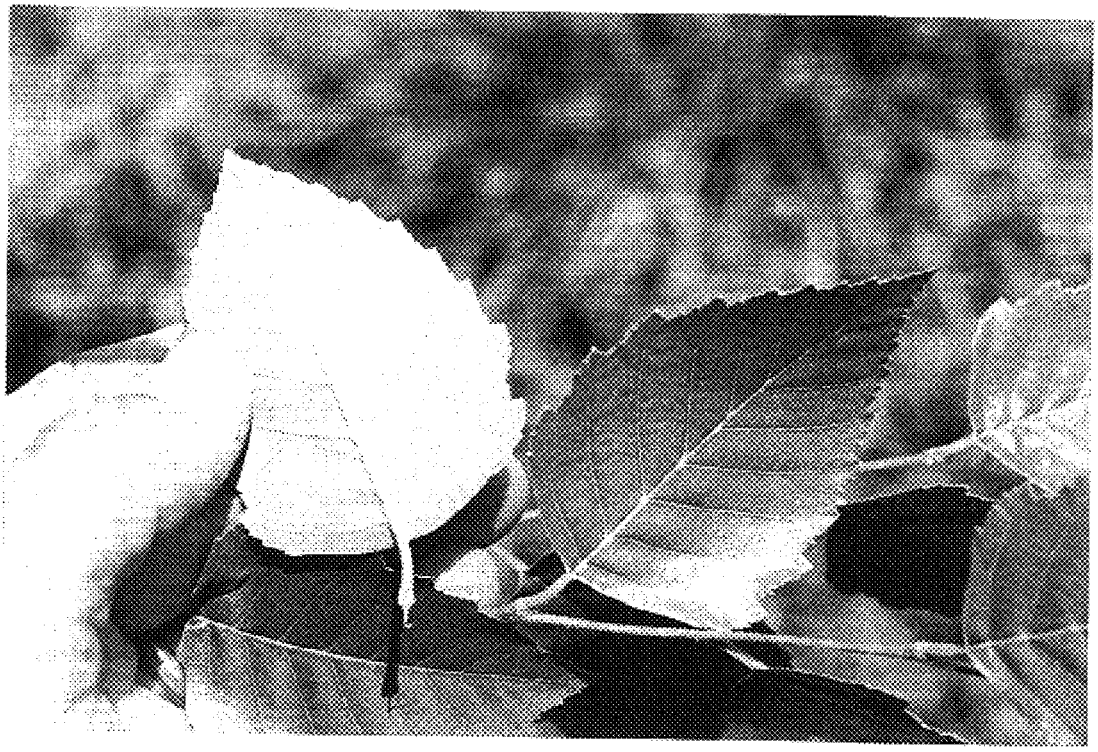
FIG. 5 is a full color photographic view of the upper and lower surfaces of mature leaves on a typical specimen of my new river birch tree.

*Shape of leaves.*—As shown in FIG. 5, the leaves are oval, short-pointed, and slightly wedge shaped at the base. Typically, the leaves have 7 to 9 main veins on each side of the midrib.

*Size of leaves.*—Typically, the leaves are between about 1.5 and about 3.0 inches long and between about 1.0 and 2.0 inches wide.

*Margins of leaves.*—Dentate, each dentate showing between about 2 and about 5 smaller serrations.

*Quantity.*—Singles that alternate on the twig.

*Color of leaves.*—During the growing season, the upper leaf surface is a shiny green (147-B or C) on young leaves and a darker green (147-A) on fully expanded leaves. The lower leaf surface is yellow-green (148-B or C) on young leaves and grey-green (191-A or B) on fully expanded leaves, with the midveins being grayish (160-A). The fall color of the leaves is yellow-gold (22-A or B).

*Surface texture of leaves.*—The upper leaf surface has a slightly rough texture that feels thick and tough. The under leaf surface has a softer texture due to pubescence distribution.

*Leaf petiole.*—The leaf petiole is between about 0.3 and about 0.6 inches long. The surface texture of the leaf petiole is similar to that of the underside of the leaf in that it is pubescent, which gives it the grayish (160-A) color.

*Stipules.*—None.

*Stems.*—The numerous stems are characterized as being slender, spreading and flexible.

*Stem color and texture.*—Young stems having a diameter less than between about 0.75 inches and 1 inch are shiny, smooth and orangey-brown (177-A or B or 200-C or D) with prominent lenticles. The number and color of lenticles is extremely variable and not different than other known cultivars of river birch trees. The color designations of the lenticles are most often in the 156-A, B, or C range but are quite variable. Stems having a diameter of between about 0.75 inches and about 1 inch and larger, typically near the end of the second growing season, have a peeling bark. The peeling bark pieces on young stems are dark tan (166-A or B). By late September, in central Oklahoma, the exposed bark on stems having diameters of between about 0.75 and about one inch or larger is creamy-white (158-C or D) and smoother than the bark found on some other river birch trees, such as the Dura-Heat® river birch tree. The bark coloration remains this color until active growth is well under way the following April or May, when the exposed bark begins to darken. For example, the old bark on the tree shown in FIG. 1 had darkened to a cream color (159-A or B).

Flowers: Male and female flowers appear in separate catkins on the same tree. The male flowers are characterized as hanging clusters of slender, shiny dark brown (166-A or B) catkins that are between about 1.5 inches and about 2.5 inches long. The female flowers are characterized as being in upright green (147-A or B) catkins that are between about 0.15 and about 0.4 inches long.

The male flowers typically appear in early to mid-April in Stillwater, Okla. and seeds reach maturity by early to late May. Female flowers appear in late April to early May. The dormant winter buds are typical of those found on other river birch trees.

Fruits: The fruits are cylinder shaped, hanging cones with tan coloring (166-A, B or C) and are between about 0.75 and about 1.5 inches long. The fruits are composed of numerous three-lobed scales, each scale enclosing a single, tiny winged seed.

I claim:

1. A new and distinct variety of a river birch tree, substantially as illustrated and described.

* * * * *